(12) United States Patent
Wong

(10) Patent No.: US 11,527,310 B2
(45) Date of Patent: Dec. 13, 2022

(54) PSEUDONYMOUS CRYPTO-BASED SYSTEMS AND METHODS FOR PATIENT DATA

(71) Applicant: Sze Yuen Wong, Herndon, VA (US)

(72) Inventor: Sze Yuen Wong, Herndon, VA (US)

( * ) Notice: Subject to any disclaimer, the term of this patent is extended or adjusted under 35 U.S.C. 154(b) by 876 days.

(21) Appl. No.: 16/176,746

(22) Filed: Oct. 31, 2018

(65) Prior Publication Data

US 2020/0135306 A1    Apr. 30, 2020

(51) Int. Cl.
*G16H 10/60* (2018.01)
*H04L 9/40* (2022.01)
*H04W 4/021* (2018.01)

(52) U.S. Cl.
CPC ......... *G16H 10/60* (2018.01); *H04L 63/0421* (2013.01); *H04W 4/021* (2013.01)

(58) Field of Classification Search
CPC .... G16H 10/60; H04L 63/0421; H04W 4/021
USPC ........................................................ 705/2–3
See application file for complete search history.

(56) References Cited

U.S. PATENT DOCUMENTS

| | | | | |
|---|---|---|---|---|
| 10,171,935 B1* | 1/2019 | Reyes | .................... | G16H 40/67 |
| 2014/0278545 A1* | 9/2014 | Andrews | ................ | G16H 10/60 705/3 |
| 2016/0063189 A1* | 3/2016 | Soon-Shiong | ......... | G16H 10/65 705/3 |
| 2016/0335686 A1* | 11/2016 | AthuluruTlrumala | ...................... | H04N 21/44222 |
| 2017/0118590 A1* | 4/2017 | Baca | ...................... | H04W 4/029 |
| 2017/0213050 A1* | 7/2017 | Ramaci | .................. | G16H 20/10 |

* cited by examiner

*Primary Examiner* — Michael Tomaszewski

(57) ABSTRACT

Systems and methods of a cipher-based system for tracking a patient within a clinical pharmacy workflow, the system includes providing a meshed network having patient devices that communicate patient data with aggregators. The patient devices and aggregators located within the space form a meshed network, the aggregators communicate data to a computer in communication with a cloud-based network. A patient device with a mobile application wirelessly communicates with an internet system in communication with the cloud-based network. Receiving by the computer, information about the user patient device entering the meshed network by wireless tags positioned within the space. Information is obtained by the patient devices during a recognition process by wirelessly transmitting messages between the wireless tags to aggregators, and then wirelessly transmitting information from the aggregators to the computer, the computer communicates with the cloud-based network, the cloud-based network communicates with healthcare administrator systems via jointly defined API interface.

17 Claims, 10 Drawing Sheets

The four basic principles of cipher-based data security:
1. Trust-No-One. Data belongs to end-users. No exceptions.
2. Distributed Repositories.
3. No system-level access keys.
4. All access-control must be crypto-based.

FIG.3

PSEUDONYMOUS CRYPTO-BASED SYSTEMS AND METHODS FOR PATIENT DATA

FIELD OF THE INVENTION

The present disclosure relates to cipher-based access control systems and methods.

BACKGROUND OF THE INVENTION

Global access to antiretroviral treatment (ART) has substantially improved over the past 15 years, according to the World Health Organization (WHO), and Zambia is no exception. Still, the country's HIV prevalence rate is high at around 12%.

671,066 Zambians were on ART—42,520 of them children. The UNAIDS Prevention Gap Report noted that another 55,000 adults and 5,000 children in Zambia were infected with HIV.

With proper treatment, HIV has become a chronic disease in Zambia and the country is on track for achieving the global 90-90-90 targets. For this to continue, though, high levels of ART adherence must be sustained.

Throughout the country, effective patient tracking and significant loss to follow-up care represent two critical challenges as Zambia works to ensure all people living with HIV (PLHIV) have access to quality treatment services and stay adherent to their ART regimens. There exists a need to make it easier for the clinical team to identify HIV-positive mothers, children, and adolescents who are having difficulties adhering to treatment.

More than 1,000 HIV clients went off treatment and were lost to follow up care. Staff needs help to identify these patients and determine their status, and track those who transferred to other health sites or died. The Family Support Unit also needs help to identify service delivery gaps in order to improve the quality of care provided to clients, and to reduce loss to follow-up among children and adolescents living with HIV.

A need exists with an increase in the number of follow ups the Unit is conducting, to save time and money in order for the clinical team to have all the necessary knowledge and technology to support their work in providing quality treatment and care to patients, to interact with more and more patients each week, to follow up and link patients to the hospital where they can access quality care and treatment.

In the age of the smartphone, clinical teams are in even greater control and want to not only track patient treatment and manage cares for them overall, but also use their phone to find out what is happening to them and how they can be assisted when they show up for clinical check-ups. For example, a hospital (or any office space, doctor's practices, etc.) often can use independent scheduling systems or integrated scheduling systems into their overall IT infrastructure. The meshed network needs to communicate with this scheduling system in order to provide the service. The patient/user must be signed into the application for identification purpose. The identity of the user needs to be protected by the application, user profiles need to be stored in databases, and personnel of the location need to be informed of medical records of the patient for verification.

By The four basic principles of data security, data-at-rest such as medical records and user profiles, should stay encrypted at all times, be portable to facilitate distribution across heterogeneous storage and protection mechanisms. Data-at-rest should be protected with baked-in security independent of its environment; eliminating any systems keys and/or lookup tables that may be misused as backdoors. If a staff member needs access to the end-user's data in order to provide support, an explicit grant is required by the end-user themselves.

With the most recent data breach, even encrypted data was compromised due to some poor decisions of storing encryption keys within the same data center, thus the hackers got access to the keys once they got in. The crypto logic is still secure, but if the key is stolen, the crypto logic is irrelevant. If you follow the trend of all the massive data breaches, you can see the hackers are getting into bigger and bigger data repositories. From retail stores, to the government, now to the very place that stores credit information. The more concentrated the data, the more profitable a successful hack is. Conventional access control system architecture follows the "trust all staff members within a given organization and allow access to most patient data." With this mindset, any weak password could potentially expose the entire data repository.

In order to protect data in the event of data breach due to weak access control, the focus should not be about building bigger and thicker firewalls. As we have seen with recent events, any individual with enough incentive and skill can get through the thickest of firewalls and get inside any system. The focus should be on making it less profitable for hackers to break into any given system. Instead of building the bigger data repositories, we should instead build a distributed system. In simplest terms, once the hackers break-in, they can access ALL of the data.

Privacy law such as The General Data Protection Regulation (GDPR) will lead to a greater degree of data protection, while at the same time requires companies handling patient data to undertake major operational reform. Strict requirements are put on systems that track patients while they receive treatments in a hospital, collects data to perform data analytics regarding their behaviors and conditions.

Prior to the GDPR, the default was that data was available for use and affirmative steps had to be taken to protect the data. For many years, businesses relied upon traditional securities to ensure that data was kept safe—these measures were things like firewalls on the network, user ID and password protection on computers etc. All these measures are external to the design of the system.

This introduces a new discipline in system design. Now we must place privacy as a key area alongside functionality. This will be a consideration very early in the design cycle to design proportional and effective protection need into the system. Such protection may be to encrypt the data before storing it or designing levels of authority so that only required fields are shown to users of a system and not everything.

Encryption is important, valuable and in many modern information and data systems present. Nevertheless, a confidentiality breach of personal data that were encrypted with a state-of-the-art algorithm is still a personal data breach. Data Protection by Default requires granular, context sensitive control over data when it is in use so that only the data proportionally necessary at any given time, and only as required to support each authorized use, is made available.

Therefore, there is a need for a mobile device tracking system that is designed from the ground up with privacy in mind, with privacy-focused features such as Pseudonymization, Data Minimization and Proportionality forming an integral part of the system features.

SUMMARY OF THE INVENTION

Patients have previously downloaded a specific mobile application running on their patient device. A radio-based system capable of saving battery power for deployed, autonomous radio emitting devices disseminated within a space to form a meshed network. The meshed network of the fixed radio emitting devices creates a geo-fence within the space, wherein the fixed radio emitting devices are capable of wirelessly communicating with neighboring fixed radio emitting devices. Upon the patient opening the specific application for that space on the patient's smart mobile device, the application can have the ability to interface with the meshed network which automatically senses when the device breaks the geo-fence it created in a particular location (indoor or outdoor) or space. The patient using the specific application (or a feature of the application) is able to be "checked" in automatically without human intervention.

Within the healthcare space, the methods and systems of the present disclosure can monitor when a patient left a room and provide notice to a cleaning service to be dispatched to make the room ready for the next guest. A hospital (or any public space, doctor's practices, etc.) often can use independent scheduling systems or integrated scheduling systems into their overall IT infrastructure. The meshed network needs to communicate with this scheduling system in order to provide the service. The scheduling system allows the personnel to make appointments for patients. A patient using a dedicated application is able to be "checked" in automatically without human intervention. The patient/user must be signed into the application with a unique ID/password combination. The identity of the user is locally encrypted by the application and also stored (encrypted) on the cloud. If the Scheduling system is integrated with the hospital's/doctor's office EMR (Electronic Medical Records), then the Scheduling system can send the patient's EMR information for verification on the patient's patient device.

As soon as the geo-fence is broken by the patient device, the iForm system sends a notification message to the healthcare Administrator system informing it that User X arrived on the premises or within the space. The healthcare Administrator system can check the identity of User X and match the records stored in its own database. If the records match, healthcare Administrator system checks in User X for his/her appointment. If Administrator system contains the EMR records of User X and if User X is allowed to preview its personal information via the application running on the mobile device, then User X can check that all personal information is correct and commit any changes made via the application running on the mobile device.

A central computer can perform functions related to applications which need to be performed. The central computer can be completely independent of the healthcare administrator systems or able to communicate with it via a jointly defined interface or an API. The central computer can also be connected with mobile applications distributed on different server devices. The applications running on iOS® or Android® or Windows® devices can be downloadable and can contain specific applications along with performing specific functions directed by the central computer.

The radio-based system incorporates communication from the fixed radio emitting patient devices and to smart mobile applications downloaded onto patient devices, e.g., smartphones, tablets, computers, etc. The identity of the user is locally encrypted by the application and also stored encrypted on the iForm Cloud. Upon entering the area defined by the meshed network, the user breaks the geo-fence established by the meshed network. As soon as the geo-fence is broken by the patient device, the iForm system sends a notification message to the administrator system informing it that User X arrived on the premises or within the space. Device1 (112A) is sensed by the user's patient device and a message is generated, via servers to the iForm Cloud with the contextual information (user ID, Device1 (112A) identifier & time stamp). The iForm Cloud ID matches the user profile it stores in its database and sends event based contextual information to the Scheduling system, which can inform the personnel of the location of the patient.

As data flows arrive at the central computer, data are filtered and transformed to enter into KeyWrap Records grouped into one or more RecordSets. Long running requests, such as The Excel Flattening feature, will access the encrypted data from the RecordSet by using a Dataflow Automation API, and be able to decrypt those Data by means of an Access Token. A nested-key design provides inherent cipher-based protection to both its data component and its decryption key component when at rest, independent of and in addition to any access control mechanisms of the environment.

BRIEF DESCRIPTION OF THE DRAWINGS

FIG. 3 illustrates the four underlying principles of cipher-based data security.

DETAILED DESCRIPTION OF THE INVENTION

Figure 1:
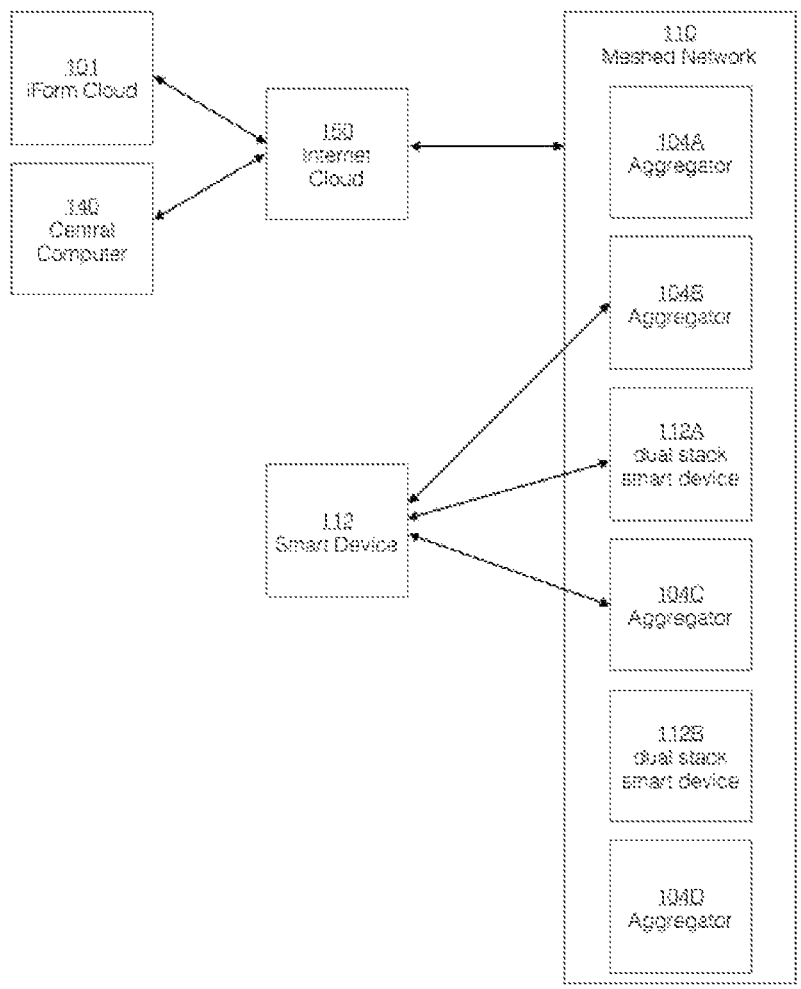
FIG. 1 illustrates a system having fixed patient devices located within the meshed network that can automatically track people and assets as they move from one position to another within the meshed network or space, according to an embodiment of the present disclosure.

Most IoT projects look to benefit from new data sources, but the vast volumes of data created by connected products can quickly drown companies, leaving them information rich and insight poor. The iForm platform offers a secure connectivity platform and messaging foundation for connected IoT devices, providing provisioning, configuration, monitoring, administration, firmware and software updates, and connected product fleet management and dashboards. The data needs to be structured and made actionable. Low latency—literally millions of messages at sub-second speed—and doing so at scale across millions of devices. The iForm platform provides device and end-user identity management capabilities to secure devices, and most importantly connected product data both in transfer and within other applications. End to end security protects both device and end user data on the device, in transit, and in the cloud—managing access, provisioning and decommissioning of a product. Remote device support allows devices to autonomously communicate issues, while providing critical context that can be used for automated or manual troubleshooting of issues on devices regardless of location. The iForm platform offers basic capabilities, such as standard APIs, and out-of-the-box connectors with these systems, which are keys to integrate connected product data with other primary enterprise systems.

Our effective cipher-based iForm and KeyWrap technologies enable companies to show that they have used privacy-enhancing technologies in accordance with reasonable data minimization, proportionality and privacy-by-design principles necessary to benefit from relaxed data breach notification rules, less strict data subject access request requirements and greater flexibility to conduct data profiling.

Innovative Key Wrapped Encryption

In a typical computer system, individual records need to be decrypted in order to be shared or regrouped. Having direct hardware or database access typically provides a backdoor to shared data in most conventional computer systems; compromising security. Our Innovative KeyWrap technologies encrypt patient data while at rest in storage, wrapped with corresponding decryption keys that are also stored in their encrypted forms. We employ proprietary cryptographic methods to ensure the presence of a matching patient key in order to decrypt the corresponding patient data for access control. A secret patient key always stays at a patient device and is never transmitted to the central server, thereby eliminating the possibility of having any backdoor methods that bypass normal authentication or encryption.

Pseudonymization

Our KeyWrap technologies provide the necessary technical measures for dynamically changing pseudonymous identifiers 218. Different RecordSet keys 217 are used to encrypt data records pertaining to a patient across multiple RecordSets 211 or data combinations. A same secret patient key (aka Entity Key) is used to encrypt each individual Entity Name 213 to obtain a unique changing pseudonymous cipher-based identifier 218 for each corresponding RecordSet 211 represented in the aggregated database. The secret patient key, as well as all tracking information, are kept separately and subject to technical and organizational measures to ensure non-attribution to an identified or identifiable patient.

Centralized Key Store Coupling with Decentralized Cipher-Based ACL

Encryption keys are key: centrally securing a RecordSet Key while in storage is considered a strong security measure. Trusted Entity List technologies, on the other hand, provides decentralized cipher-based ACL protection for run-time execution. The two innovative technologies complement each other to form a tracking system wherein privacy protection is baked in to be applied at earliest opportunity.

Proportionality

Since RecordSets are individually encrypted and wrapped with a corresponding RecordSet Key, proportionality is inherently supported, where data pertaining to a patient is only accessible with a matching secret patient key, thereby preventing all unauthorized use without a patient's authorization. Granular, context sensitive control over data when it is in use so that only the data proportionally necessary at any given time, and only as required to support each authorized use, is made available. Any information whose processing is not necessary to provide the service requested by the end-user is protected with state of the art security measures applied from end to end, including cryptographic methods such as encryption.

Secondary Use and Data Analytics

The Act defines the secondary use of data as the use of data for purposes other than for what it was originally collected for. These GDPR requirements for specific and unambiguous consent are impossible to satisfy in the case of iterative data analytics where successive analysis, correlations and computations are not capable of being described with specificity and lack of ambiguity at the time of consent. Under the GDPR, broad consent no longer provides sufficient legal basis for data analytics or use of historical databases involving personal data. As a result, data controllers and processors must adopt new technical safeguards to satisfy an alternate legal basis.

Pseudonymization may facilitate processing personal data beyond original collection purposes. Article 5 provides an exception to the purpose limitation principle, however. The GDPR allows controllers who pseudonymize personal data more leeway to process the data for a different purpose than the one for which they were collected. GDPR requirements may be satisfied by complying with new Pseudonymisation and Data Protection by Default requirements to help support alternate (non-consent) legal bases for analytics.

Pseudonymisation and Data Protection by Default help to satisfy alternate (non-consent) legal bases for data analytics involving EU personal data. Specifically, controllers must adopt "technical and organizational measures" to adhere to the data minimization principle. The only example the Regulation provides is for controllers to use pseudonymization so that the processing "does not permit or no longer permits the identification of patients."

Our KeyWrap technologies provide the necessary technical measures for an organization to adhere to the data minimization principle and proportionality. Specifically, our key technologies support dynamically changing pseudonymous identifiers 218. Unique RecordSet keys 211 are used to encrypt respective entity names 213 pertaining to a patient across multiple RecordSets 211 or data combinations, wherein a same patient key is used to encrypt each of the RecordSet keys 217 resulting in changing pseudonymous identifiers 218 unique across a patient's RecordSets. Further, an entity name 213 included in a RecordSet 211 is encrypted by using a RecordSet key 217 included in the same RecordSet 211 resulting in a ciphertext 218 unique across a plurality of RecordSets pertaining to the patient. Since RecordSets 211 are individually wrapped and can only be accessed with a secret patient key, proportionality is inherently supported in our invention.

Pseudonymization and Data Protection by Default

GDPR imposes a new mandate to provide Data Protection by Default, which goes further than providing perimeter only protection and is much more than merely "privacy by design." Data Protection by Default requires that data protection be applied at the earliest opportunity (e.g., by dynamically Pseudonymizing data) and requires that steps be affirmatively taken to make use of personal data. This is in stark contrast to common practices prior to the GDPR, when the default was that data was available for use and affirmative steps had to be taken to protect the data. Data Protection by Default requires granular, context sensitive control over data when it is in use so that only the data proportionally necessary at any given time, and only as required to support each authorized use, is made available.

To pseudonymize a RecordSet, the "additional information" must be "kept separately and subject to technical and organizational measures to ensure non-attribution to an identified or identifiable person.", including online identifiers provided by their devices, applications, tools and protocols, such as internet protocol addresses, cookie identifiers or other identifiers such as radio frequency identification tags. This may leave traces which, in particular when combined with unique identifiers and other information received by the servers, may be used to create profiles of the natural persons and identify them.

The GDPR recognizes that static (persistent) purportedly "anonymous" identifiers used to "tokenize" or replace identifiers are ineffective in protecting privacy. Due to increases in volume, variety and velocity of data combined with advances in technology, static identifiers can be linked or readily linkable leading to unauthorized re-identification of patients.

A critical element of an IoT solution is a centralized system of record to manage users and groups of connected products. In itself, organizing users for access and authentication is complex and can become an unmanageable process. Identity management is a critical element of any connected product system. iForm platform offers pre-configured permissions and organization hierarchies included with the platform to securely manage important elements such as users and devices, onboarding flows and data visibility, provide a unique set of credentials for every device to protect against vulnerabilities or unauthorized attempts to tamper with device information. iForm platform offers a unified system of record and set authorizations at the user of device level for seamlessly managing administrators and other users, configuring simple single-user or device scenarios, instances of multiple users or devices, or even complex hierarchies.

FIG. 1 shows a system having fixed patient devices 102 located within a meshed network that can automatically track people and assets as they move from one position to another within the meshed network or space. For example, the fixed patient devices 112 can be equipped with dual stack and/or be an aggregator 104 that are used to provide the function of automatically tracking people and assets as they move from one position to another within the meshed network or space. It is possible the moving objects can be attached to patient devices 112 without the dual stack. It is noted that moving objects can be detected by either dual stack patient devices and/or aggregators. A regular patient device can be attached to any moving objects which will be tracked within the area defined by a meshed network representing a group of patient devices within the meshed network or space. For instance, medical devices moving from one operating room to another, handicap scooter, computers on rollways, etc.

Every time a patient device moves, the fixed aggregators read its signal strength. To determine whether a patient device is closer from a specific fixed aggregator (or dual stack patient device), radio frequency signal triangulation is used based on the calibration data provided to a central computer that is in communication with a cloud-based network. If the radio frequency signal of the patient device can only be "heard" by two fixed aggregators, then the determination is made based on the relative signal strength heard by the two aggregators.

Every time a patient device was determined to have a new location, a time stamp is recorded at the time the event occurred and stored in the central computer for further processing. The central computer (or iForm Cloud) can also send event push notifications to smart mobile devices registered to receive events for specific patient device IDs.

Figure 2:
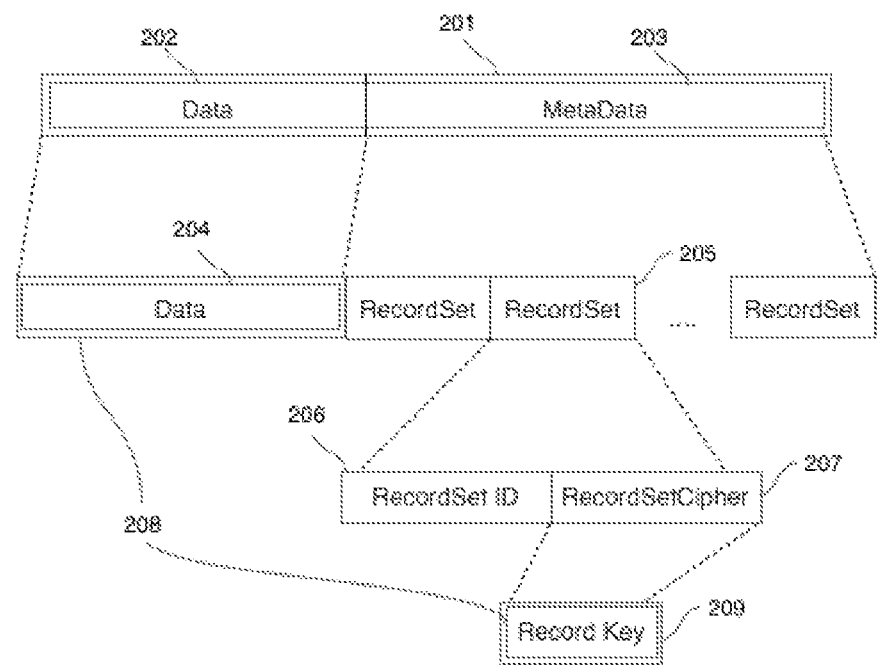
FIG. 2 illustrates a KeyWrap Record diagram.

FIG. 2 illustrates a KeyWrap Record 201 and the four underlying principles of cipher-based data security to its architecture. In a KeyWrap Record 201, a Data component 202 is coupled with its Decryption Key components 203 to form a composite data structure 201, representing a most atomic data representation unit in the architecture. Both components stay encrypted at rest. A Decryption Key component 203 is protected by a separate RecordSet Key 217. Thus, a Data component 202 is protected from improper access to a KeyWrap Record 201 without having obtained access to its corresponding RecordSet Key 217. Implemented as a JSON structure, a KeyWrap Record 201 is highly portable, allowing straightforward distribution across heterogeneous storage and protection mechanisms. A nested-key design provides inherent cipher-based protection to both its data component 202 and its decryption key component 203 when at rest, and it offers protection in a way that is independent of and in addition to any access control mechanisms happen to be offered by a destined storage system, thereby eliminating any risk of having dependencies on any weak access control protection external to the KeyWrap Record 201. System keys and/or lookup tables are eliminated by design, thereby enhancing protection from weak username and passwords, as well as maintaining trust and integrity if and when distributed across access control systems disparate in quality and character.

The RecordSet 211 is logical groups of records. The RecordSet 211 usually represents all records 201 within a Table (in RDBMS) or Collection (in document or key-value stores) but can also be defined to represent a much smaller or larger set of records.

The RecordSet 211 maintains a list of trusted entities. The Trusted Entity List is used for sharing and access control. The Trusted Entity list may contain one or more Entity References 219. The Entity Reference 219 is referring to Entity record, that has access to the particular RecordSet 211. When an entity is being assigned to RecordSet 211, that Entity Reference 219 is added to the Trusted Entities list.

The Entity Reference 219 contains 3 sections: Entity Name 213, Access Level, and RecordSetKeyCipher. The Entity Name 213 is the name of the entity that has access to the RecordSet 211. The Access Level indicates the abilities the entity can perform on the RecordSet 211. The Access Level can have the value of either READONLY or READWRITE. The RecordSetKeyCipher is essentially the encrypted RecordSet key 217. The RecordSet key 217 is a random generated key that was created when the RecordSet 211 got created. The RecordSet key 217 is encrypted by the Entity key to form the RecordSetKeyCipher.

The Record 201 serves as a basic container where the data portion 204 is protected via the key wrapping mechanism of the invention. The Record 201 data structure is divided into two sections: Record Data 202 and Record MetaData 203.

Data 204 in the Record Data section 202 is protected by a Record key 209. The Record key 209 is generated during record 201 creation time and will stay with the record 201 for the life-time of the record 201. The purpose of having individual Record keys 209 is so that the records 201 do not need to be decrypted when sharing records, or during regrouping.

The Record MetaData 203 section may contain one or more RecordSet References 205. The RecordSet Reference 205 is referring to a logical group of Records 201 which is known as RecordSet 211 in this invention. The implication is that each Record 201 can belong to multiple logical groups. Data sharing and data access control is being controlled via the use of the RecordSet Reference 205. The Record 201 can be shared to multiple users/entities. The Entity would only have access to records based on the RecordSet 211 that the entity belongs to.

Each RecordSet Reference 205 contains the RecordSetId 206 and the RecordKeyCipher 207. The RecordSetId 206 identifies the RecordSet 211 that Record 201 belongs to. The Record key 208 is encrypted by the RecordSet key 217 to form the RecordKeyCipher 209. The RecordKeyCipher 209 is stored in the Record MetaData 203 section and will be used with the RecordSet key 217 to obtain the Record key 208 to unlock the encrypted data 202.

As data arrive at the central computer, data are filtered and transformed to enter into KeyWrap Records 201 grouped into one or more RecordSets 211. An iForm aggregate API is called to retrieve Page, Element, Option List, and Options information from the mobile application. The API can be called one time during setup or runtime (everytime the data enter the RecordSet 211) to transform the data accordingly based on the option selected above. Long running requests, such as The Excel Flattening feature, will access the encrypted data from the RecordSet 211 by using a Dataflow Automation API, and be able to decrypt those Data by means of an Access Token. Dataflow Automation is an entirely separate service that will store Flattened/Transformed data into RecordSet 211. In one embodiment, the Excel Service became one of the Post Actions for Dataflow Automation to insert data into an excel file one record at a time via an Excel library. In another embodiment, the Excel Service insert all records to the Excel file all at once. Data are not being passed through the Excel service API. Instead, the Dataflow Id, RecordSet Id are being passed.

Figure 2B:
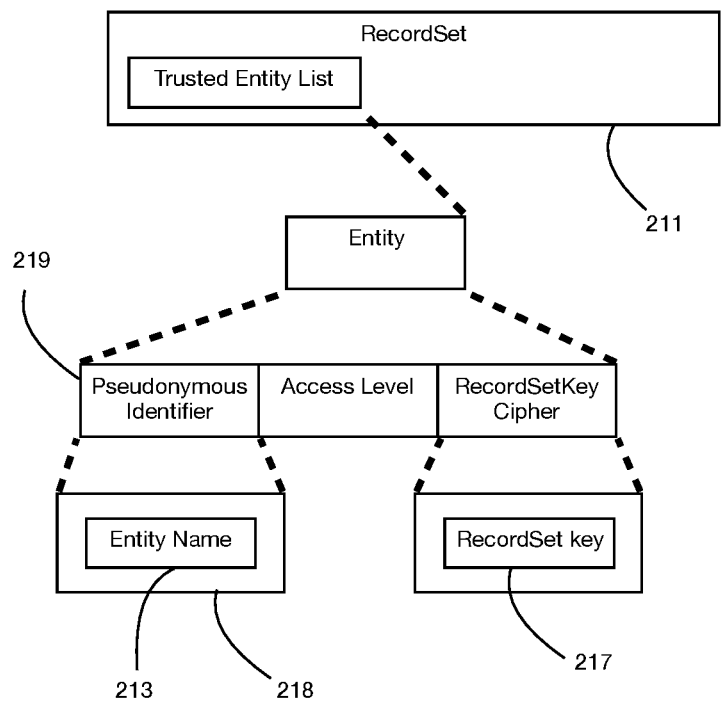
FIG. 2B illustrates a KeyWrap RecordSet diagram.

With a lack of local storage, IoT devices need to utilize the cloud. A robust data center is needed as well as controlled access of data. iForm platform offers time-series data storage as a baseline of the standard platform. The iForm database is an object database. Conceptually, the objects can be represented as JSON objects. Multi-record Subform need to be in its own tab (in Excel). A subform structure having one or more page records can be shown in the same tab or separate tabs, where options to handle subform structure will be shown in a field on a admin UI. A multi-record subform will be implemented as a sub-JSON-object for storage in one or more RecordSets. Each object has a unique identifier in the form of a GUID. A schema is defined by templates and custom fields. If the schema needs to be extended with custom entities, an external database can be used. The database can be relational or non-relational, depending on application requirements. For example, a custom schema that aligns with other business systems can be defined to collect data from devices with that schema in an external relational database, and deposit data collected from devices into these tables. iForm database and external databases can be linked with foreign keys. For example, a one-to-many relationship between an iForm entity and an external entity can be represented by using a foreign key in the external database, where the foreign key is the iForm entity ID (the UUID). For a one-to-many relationship from the external database to iForm platform, the foreign key would be on the iForm side, so it would be defined as a custom field for the iForm entity. FIG. 2B illustrates a KeyWrap RecordSet. For purpose of keeping RecordSets 211 pseudonymous, each entity name or ID 213 is stored encrypted by using a respective RecordSet key 217 in the same RecordSet 211, such that each RecordSet 211 pertaining to the same patient will have a unique ciphertext 218 for the entity name or ID. Further, an entity name 213 included in a RecordSet 211 is encrypted by using a RecordSet key 217 included in the same RecordSet 211 to result in a ciphertext 218 unique across a plurality of RecordSets 211 pertaining to a patient.

IoT connected devices continuously, and very rapidly, generate a large volume of data. To process this streaming data, it must be ingested sequentially and with a low latency. iForm platform offers a number of tools to accomplish comprehensive data management. A distributed queue is used to poll for work items. It's robust and allows a system to control resource usage by determining when to poll, lowering the risk of a system being easily overwhelmed by fast incoming data feeds. High performance message infrastructure is used for meeting an exponential growth in data. As a request coming in, the request is added to a RabbitMQ broker to ensure the order of subtasks. When the consumer consumes a message from the RabbitMQ broker, it will create a child process. A child process will be used to retrieve data from Dataflow Automation API and write them into an excel file. The broker is designed for scalability to very large numbers of devices and message rates, while providing extremely low latencies. Under security considerations to maintain privileged data access control to an owner, a polling process in a typical high scalability architecture has a need of some kind of access token for data exchange among processing services. Available for both iOS and Android, iForm SDKs provide structure and methods for interacting with the iForm platform, including messaging and platform API calls.

In order to take advantage of leverage that can be found in KeyWrap technology, computation will need to flow to a specialized security cloud for a certain operation that requires high security. If the application has a large computation it needs to carry out, then it will need to find and make use of certain network routes to lower latency to a predefined threshold. Data from device sensors is sent over channels. Polling is bad because applications have a fixed free daily quota for consumed resources, when the number of data channels the service processed increased—the daily quota was exhausted before the end of the day because it tries approximate real-time with frequent polling of the service for each channel. Typically, each sensor belonging to a particular device has its own channel, but channels also may be used by applications to partition message traffic, for example by flags in the message payload. A separate filtering service is devised to process channels. For purpose of optimal use of network resource in high load and high availability environments, filtering services should be applied as close to the publisher as possible to keep number of notifications that nobody wants to a minimum. Likewise, processing services should be applied as close to the consumer so that the original update may be transported through the network as a single notification for as long as possible. Real-time stream processing tools and rules engine can be used to perform root cause analysis, create visualizations and post massive queries.

Figure 4A:
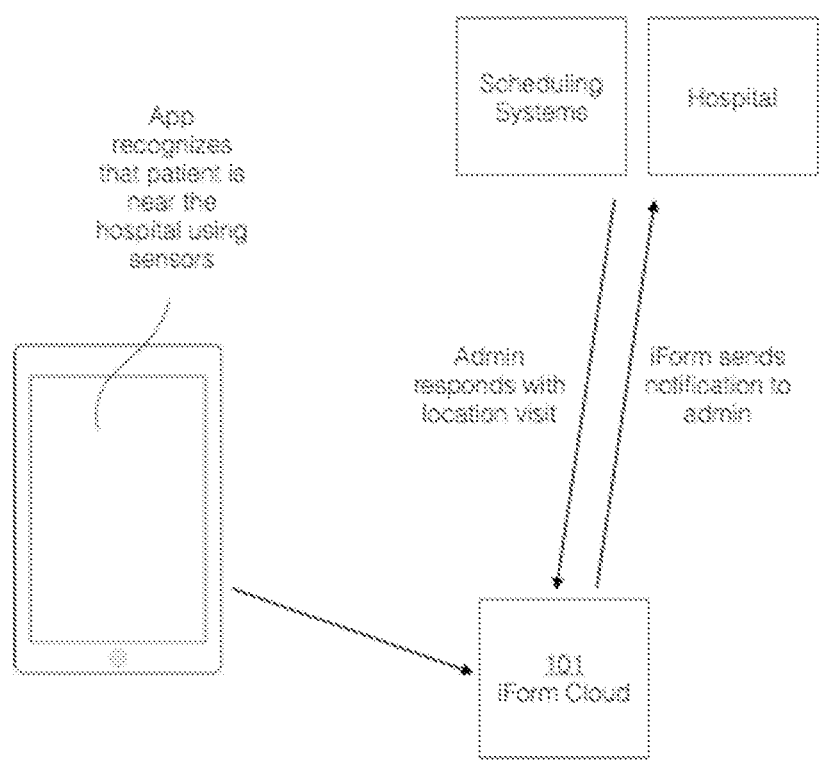
FIG. 4A illustrates a system that can be connected to a healthcare Administrator system in charge of appointment scheduling for patients within the healthcare industry, according to an embodiment of the present disclosure.
Figure 4B:
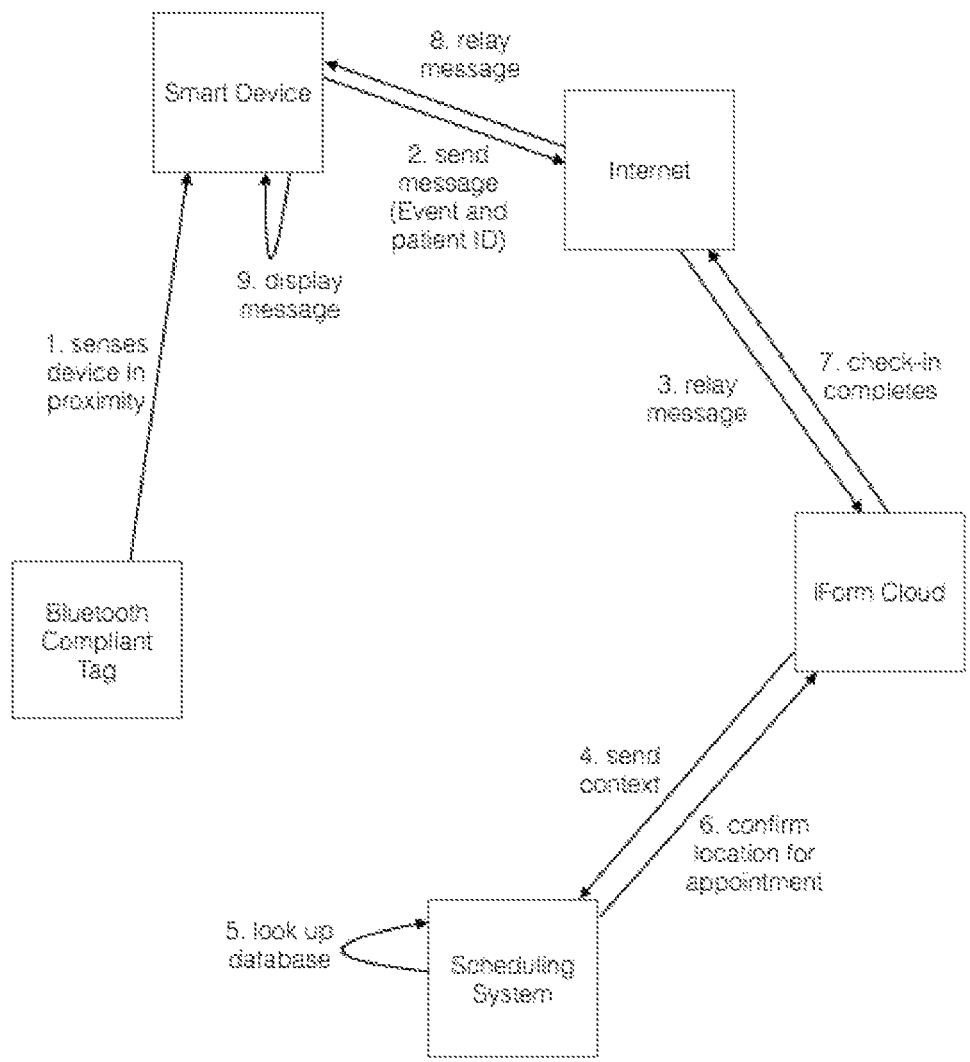
FIG. 4B is a flow diagram illustrating the steps for connecting the system to a healthcare Administrator system in charge of appointment scheduling for patients within the healthcare industry, according to an embodiment of the present disclosure.

Referring to FIG. 4A and FIG. 4B, in a previously described meshed network, a user using a mobile device can be running a specific mobile application. This specific mobile application can have the ability to interface with the meshed network which automatically senses when the device breaks the geo-fence it created in a particular location (indoor or outdoor) or space.

FIG. 4A illustrates a system connected to a healthcare scheduling system in charge of appointment scheduling for patients within the healthcare industry. For example, a hospital (or any office space, doctor's practices, etc.) often can use independent scheduling systems or integrated scheduling systems into their overall IT infrastructure. The meshed network needs to communicate with this scheduling system in order to provide the service. The scheduling system allows the personnel to make appointments for patients. In the meshed network of the present disclosure, a patient using a dedicated application (or a feature of the application) is able to be "checked" in automatically without human intervention. The patient/user must be signed into the application with a unique ID/password combination. The identity of the user is locally encrypted by the application and also stored (encrypted) on the iForm Cloud 101. Upon entering the area defined by the meshed network, the user breaks the geo-fence established by the meshed network. Device1 (112A) is sensed by the user's patient device and a message is generated, via servers to the iForm Cloud 101 with the contextual information (user ID, Device1 (112A) identifier & time stamp). The iForm Cloud ID matches the user profile it stores in its database and sends event based contextual information to the Scheduling system, which can inform the personnel of the location of the patient/user. This process can be repeated multiple times, every time an aggregator/Dual Stack patient device detects the patient/user on his way to the final destination. Upon reaching the final destination defined in the application running on the patient device by the location of the last aggregator reached (e.g. Urology, X-Ray, etc.), the meshed network sends the Scheduling system a new message indicating that the patient/user reached the destination. At that point, the Scheduling system can set the status of the patient/user as "checked in". If the Scheduling system is integrated with the hospital's/doctor's office EMR (Electronic Medical Records), then the Scheduling system can send the patient's EMR information for verification on the patient's patient device. The patient device will apply a patient key to each RecordSets 211 included in the received EMR to determine authorization. For the purpose of proportionality, the patient device is deemed to have authorized use of a RecordSet 211 if the applying of a patient key successfully yields an associated RecordSet key 217 via decryption, wherein the patient device would be deemed to lack authorization for using a RecordSet 211 if the decryption attempt does not succeed. Further, in order to adhere to the data minimization principle, each EMR RecordSet 211 is stored encrypted in the central server and is transmitted to the same patient device only as required to support each authorized use. If the records are unchanged, the patient simply "confirms" that the information is correct using the application. If the information is obsolete, the patient can modify and input updates (such as new address, new insurance information, etc.) using the application on its patient device and "commit" changes which will be saved in the EMR.

The user can have already downloaded a correct healthcare application on their patient device that uniquely identifies each patient, for example by a user ID & Password.

As soon as the geo-fence is broken by the patient device, the iForm system sends a notification message to the healthcare Administrator system informing it that User X arrived on the premises or within the space. The healthcare Administrator system can check the identity of User X and match the records stored in its own database. If the records match, healthcare Administrator system checks in User X for his/her appointment. Patent identities are stored in a database separate from the EMR records for secondary use and de-identification purpose.

If Administrator system contains the EMR records of User X and if User X is allowed to preview its personal information via the application running on the mobile device, then User X can check that all personal information is correct and commit any changes made via the application running on the mobile device. As such, the overall system architecture and design maintains granular, context sensitive control over data when it is in use so that only the data proportionally necessary at any given time, and only as required to support each authorized use, is made available.

FIG. 4B is a flow diagram illustrating the steps for connecting the system to a healthcare Administrator system in charge of appointment scheduling for patients within the healthcare industry.

Figure 4C:
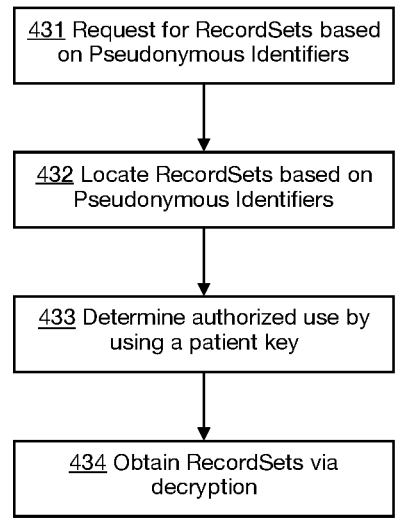
FIG. 4C is a flow diagram illustrating the steps for requesting for a respective portion of a plurality of RecordSets based on a plurality of pseudonymous identifiers.

FIG. 4C is a flow diagram illustrating the steps for requesting for a respective portion of a plurality of EMR RecordSets based on a plurality of pseudonymous identifiers 431. An application on a patient device makes a request for a plurality of EMR RecordSets pertaining to a patient and that is proportionally necessary for an application. The application provides pseudonymous identifiers to the central server to obtain a respective portion of EMR RecordSets identified by the pseudonymous identifiers 432. The application on the patient device applies a patient key to each RecordSet included in the received EMR to determine authorization. For the purpose of proportionality, the application is deemed to have authorized use of an EMR RecordSet if the applying of the patient key successfully yields an associated RecordSet key via decryption 433, in which case the application is granted access to the RecordSet 434. On another hand, the application would be deemed to lack authorization for using an EMR RecordSet if the decryption attempt does not succeed. Further, in order to adhere to the data minimization principle, each EMR RecordSet is stored encrypted in the central server and is transmitted to the same patient device only as required to support each authorized use.

Figure 5:
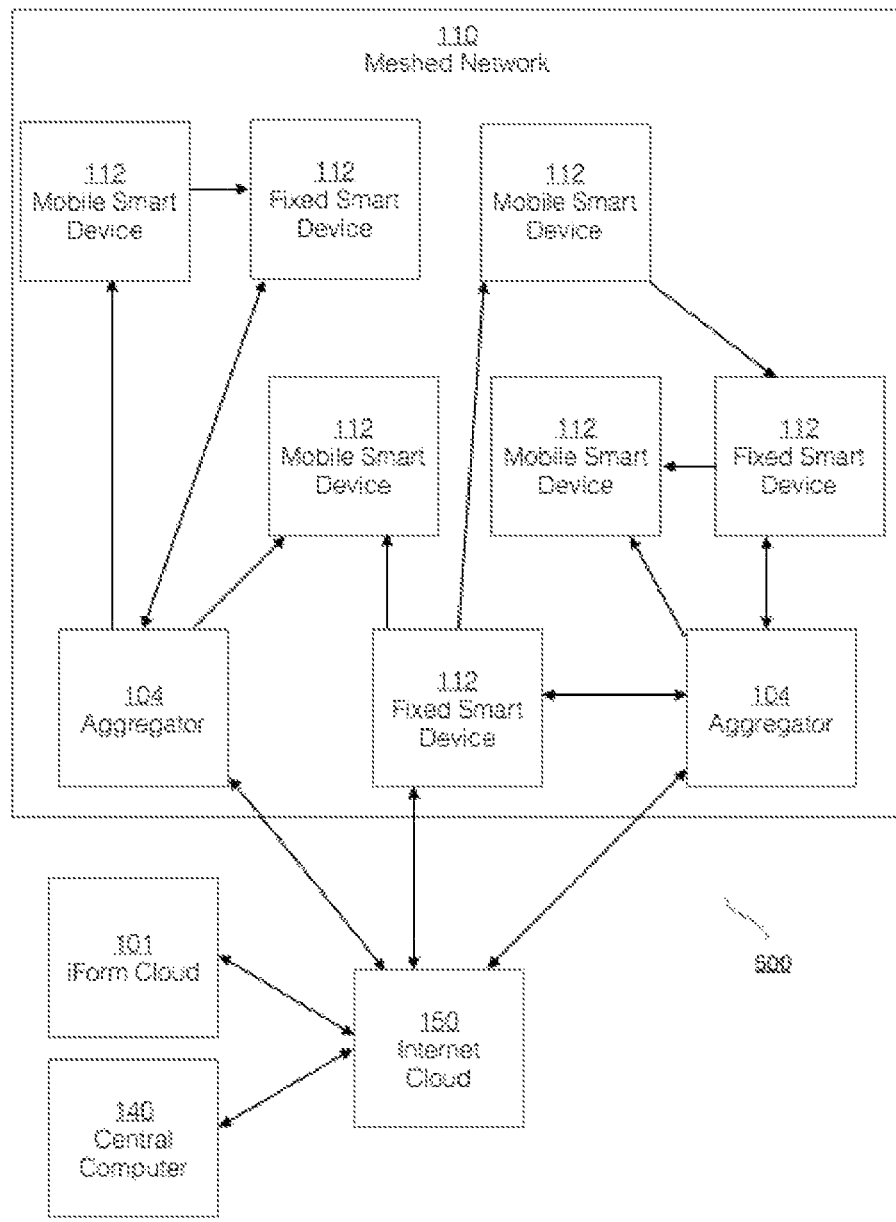
FIG. 5 illustrate patient devices and aggregators of the system structure that can communicate within the meshed network and the central computer, according to an embodiment of the present disclosure.

FIG. 5 illustrate patient devices 112 and aggregators 104 of the system structure 500 that can communicate within a meshed network 110 and the central computer 140. Patients have previously downloaded a hospital specific mobile application running on their patient device. Some aspects of the patient devices 112 and aggregators 104 include the ability to "know" when a smart mobile application is active and to "know" the relative location of the interacting device or patient device within a geo-fence or meshed network in the space. As soon as the geo-fence is broken by the patient device, the iForm system sends a notification message to the healthcare administrator system informing it that User X arrived on the premises or within the space. A user must be signed into the application with a unique ID/password combination. The identity of the user is locally encrypted by the application and also stored (encrypted) on the iForm Cloud. Upon entering the area defined by the meshed network, the user breaks the geo-fence established by the meshed network. Device1 (112A) is sensed by the user's patient device and a message is generated, via servers to the iForm Cloud with the contextual information (user ID, Device1 (112A) identifier & time stamp). The iForm Cloud ID matches the user profile it stores in its database and sends event based contextual information to the healthcare administrator system, which can inform the personnel of the location of the patient. The iForm Cloud can be completely independent of the healthcare administrator systems or able to communicate with it via a jointly defined interface or an API. The patient can decide to identify itself by providing a login information via the application or decide to be anonymous. If the login is provided, the hospital can push personalized, location-based messages to the patient. The healthcare administrator system can check the identity of User X and match the records stored in its own database. If the records match, healthcare administrator system checks in User X for his/her visit. If administrator system contains the personal records of User X and if User X is allowed to preview its personal information via the application running on the mobile device, then User X can check that all personal information is correct and commit any changes made via the application running on the mobile device.

There are different types of aggregators 104 that may be incorporated in the methods and systems of the present disclosure. For example, there can be aggregators 104 including stationary aggregators, mobile aggregators or aggregators that can communicate with hardware through software. Aggregators 104 can have one or more of the following functions in communicating with patient devices 112 within the meshed network 110 and the central computer 140. For example, aggregators 104 may: (a) read and store the radio power level of each of the patient devices 112 it connects to; (b) dynamically instruct the patient devices 112 to transmit power; (c) dynamically instruct the patient devices 112 of the frequency of their signal; and (d) push new firmware version(s) to the patient devices 112. It is noted that there can be at least two ways for implementation: (1) first, where the aggregators can be "dumb" and only transmit data and commands back and forth between patient devices and central computer. Further, this is the centralized architecture which can require more signaling between all entities, so more battery power is used; (2) second, the other way can be push intelligence into the aggregators in order for them to take some decisions locally, without the overhead messaging required with the central computer (this is the distributed architecture).

Figure 6A:
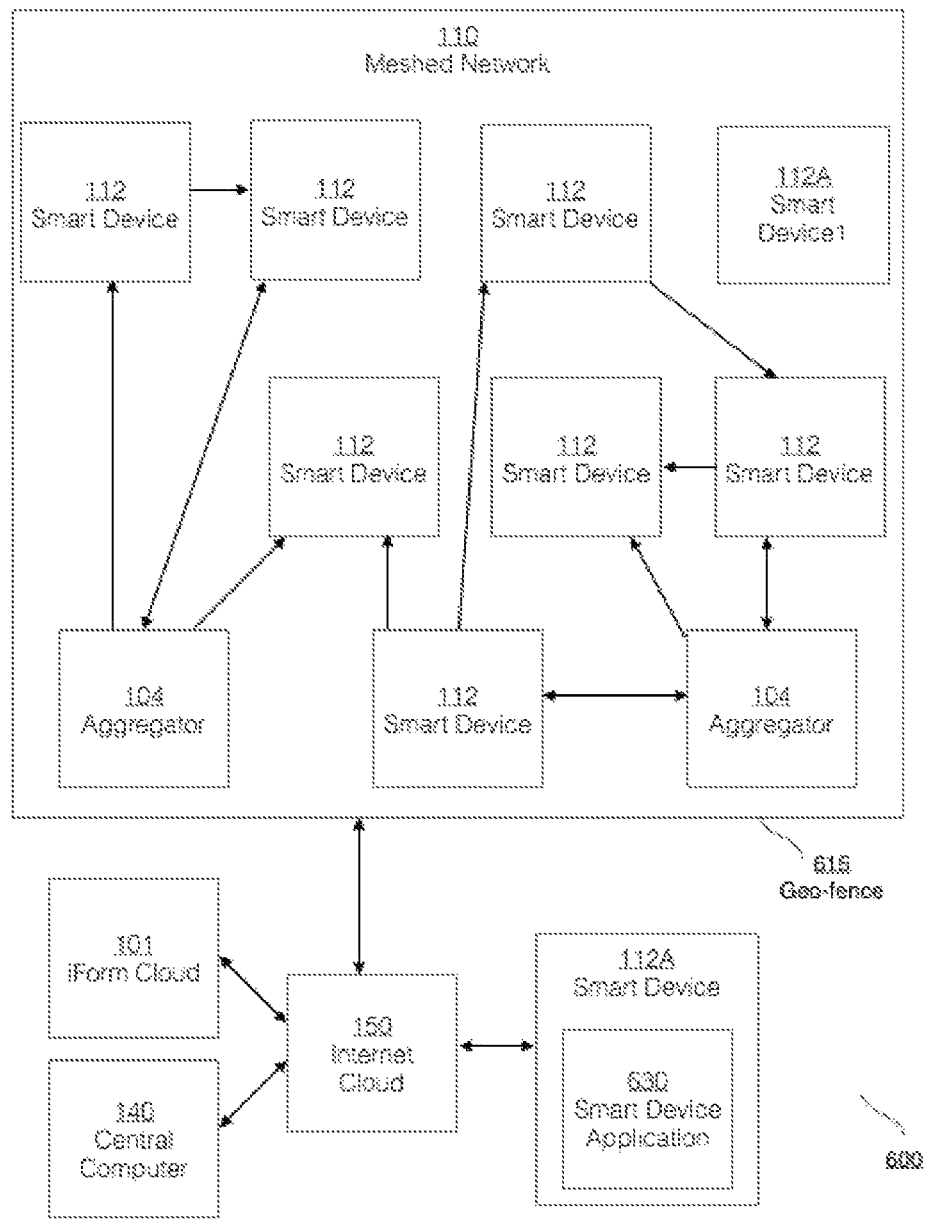
FIG. 6A illustrates an embodiment of a radio-based system capable of saving power for deployed, autonomous radio emitting devices disseminated within a space to form a geo-fence or meshed network, according to an embodiment of the present disclosure.

FIG. 6A illustrates an embodiment of a radio-based system 600 capable of saving battery power for deployed, autonomous radio emitting devices (meshed network 110 including patient devices 112, aggregators 104 and at least one Device1 112A) disseminated within a space 615 to form a geo-fence. The meshed network includes fixed patient devices 112 and aggregators 104 positioned strategically in the space 615, wherein the patient devices 112 and aggregators 104 wirelessly communicate with neighboring fixed patient devices 112 and aggregators 104 to form a meshed network 110. The fixed patient devices 112 communicate with aggregators 104 to connect to a central computer 140 that is in communication with a cloud-based network 150 via the internet. The radio-based system 600 incorporates communication data gathered from the fixed patient devices 112 via aggregators 104 through the central computer 140, the cloud-based network 150 to smart mobile applications 630 downloaded onto patient devices 112A.

Figure 6B:
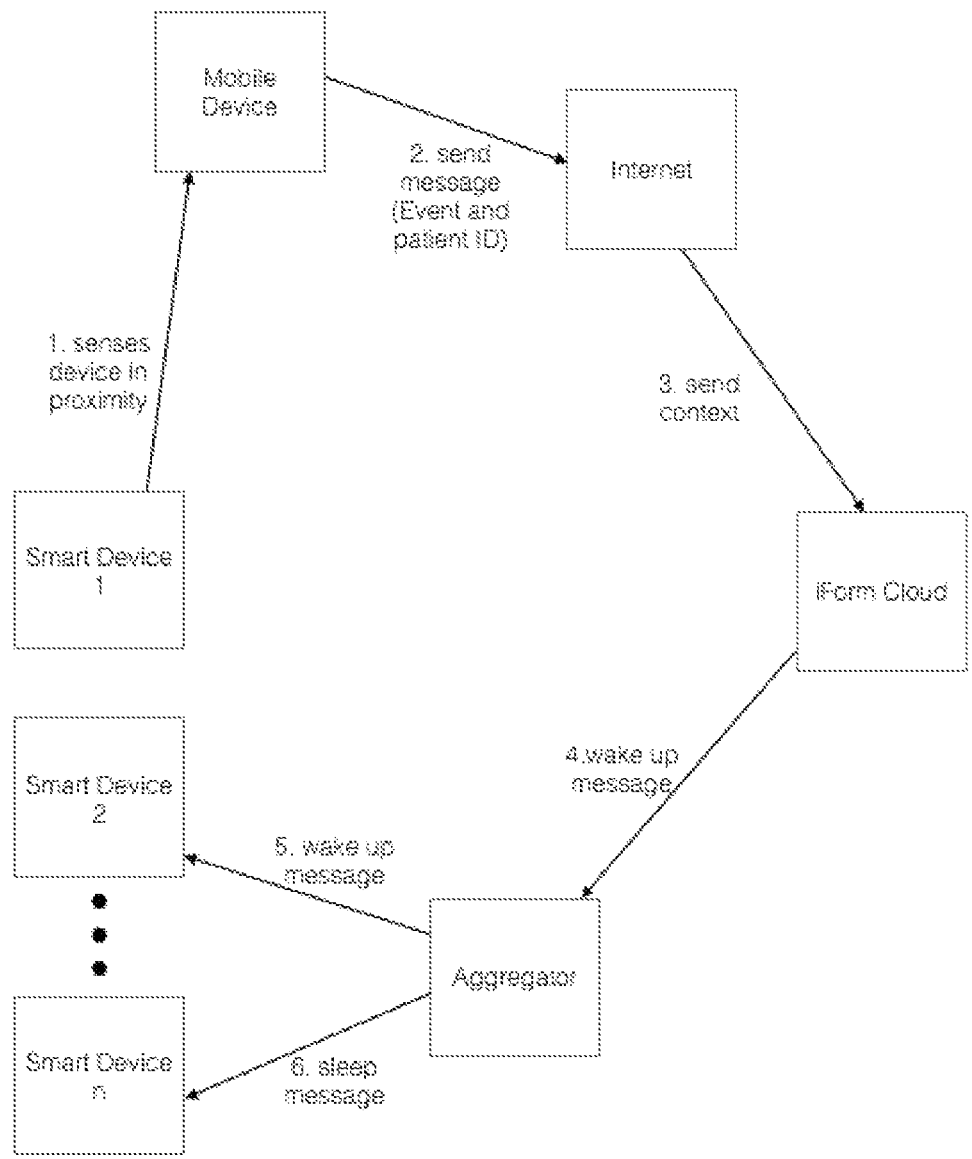
FIG. 6B illustrates an embodiment of the radio-based system, after physically placing the patient devices and aggregators within the space to form the meshed network, where power is later provided to the patient devices and aggregators so the geo-fence or meshed network can be set up, according to an embodiment of the present disclosure.

Referring to FIG. 6B, after physically placing the patient devices 112 and aggregators 104 within the space 615 to form the meshed network 110, power can be provided to the patient devices 112 and aggregators 104 so the geo-fence 615 can be set up. For example, after patient devices 112 and aggregators 104 have been placed in a fixed position and power is applied, each patient device 112 and aggregator 104 starts emitting its beacon signal with the maximum transmitting power (i.e. active state). The neighbor beacon listens to all of the beacon signals coming from all of the deployed patient devices 112 and aggregators 104 and sends the values it recorded to the gateway, i.e. Device1 112A.

During this initial startup process, the system 600 begins building a map or the geo-fence or meshed network 110. For example, the aggregators 104 "know" the location of each patient device 112, i.e. each patient device 112 has an ID which it uses in its broadcast. Once the aggregators 104 record the RF powers from each patient device 112 regarding the values it recorded from all other patient devices 112, the central computer 140 can begin to: (1) build a map with a neighbor list for each one of the patient devices 112 and their respective value, for instance, the central computer 140 can decide to keep, e.g., four (4) neighbors for each patient device 112 with an associated signal strength; (2) the central computer 140 can use a learning algorithm to compute the mean and standard deviation for 95% confidence level for each neighbor patient device 112 in the list. For example, depending of the mean and standard deviation values, the central computer 140 will assign a relative threshold level for, in a one to one relationship, in order to increase maximum likelihood for a location of a patient device 112 to be computed with a high degree of certainty.

In the initial operation of the system 600, the Device1 112A will sense that a patient device 112A broke the geo-fence it created earlier (i.e. the patient device 112A needs to be approximate the meshed network). The mobile application 630 running on the patient device 112A receives the Device1 112A signal and sends a message over cellular network to the servers communicating with the central computer 140, informing the central computer 140 that it is running a certain mobile application. The servers forward the message to the central computer 140, with the context received from the application 630 running on the Smart Mobile Device 112A. The central computer 140 sends a wakeup message to a patient device 112 or aggregator 104 where Device1 112A is registered to belong. The patient device 112 or aggregator 104 sends a wakeup message to all neighboring patient devices 112 approximate the Device1 112A to place them in a wake-up state. After the smart mobile device 112A passes the area covered by the n patient devices, the aggregator (or neighbor patient devices) send a SLEEP message to all n patient devices to resume sleep mode.

A patient device can include a wireless transceiver, processor and it can include its own power supply. For example, patient devices generally can have a Tx/Rx radio front end and the ability to "listen" to its neighbor beacons in order to adjust its power based on surrounding radio activity. A group of patient devices within a space forms a meshed network. It is noted that patient devices can also adjust their Tx power and the transmission interval when instructed through the aggregators by the cloud computer.

Some types of features of patient devices may include: (1) Bluetooth tags having HW/SW elements which are fixed or mobile; (2) Dual-stack tag having a dual Bluetooth stack able to simultaneously receive on one and transmit on the other; (3) patient devices communicating with aggregators incorporating multi functions; (4) patient devices communicating by itself or through other devices with a central computer and (5) patient devices communicating through other devices (i.e. aggregators, central computer, cloud network) to communicate with an application running on mobile devices. Aggregators can generally communicate with patient devices, patient device applications, network clouds and provide its own data/information that may be needed for operation via the specific application. Further, the Aggregators 104 can provide information to users and/or get information from users through a graphical user interface or the like. A patient device application can generally act as a control, location estimation and processing unit for the system. The application may be able to use existing hardware and software of a patient device. The central computer may be located anywhere as long as it is connected to the Internet. Further, the central computer can perform functions related to applications which need to be performed and can also be connected with mobile applications distributed on different server devices. A cloud-based network system or a network cloud can generally be defined as able to provide data storage, processing, and analytics along with other functioning aspects. For example, the system can provide notice alarms, backup data protocols for system data, synchronization and sharing of data between devices and networks, crowd mapping of identified devices and interfacing with the system via cloud-based applications. A meshed network can generally be considered as a type of network topology in which a device, tag or node can transmit its own data as well as serves as a relay for other tags or nodes located near it. The tags or nodes can be wireless using routers to provide for an efficient data transfer path for effective communication. It is noted that the nodes (or aggregators in the meshed network) can also be linked to the internet and the cloud computer via a wireless or Ethernet network.

A radio emitting device comprises a processor; a transceiver for communicating with other radio emitting devices and for communicating with an aggregator in communication with a central server computer over a network; and a storage medium for tangibly storing thereon program logic for execution by the processor, the program logic comprising radio emitting device communicating logic executed by the processor for communicating with a plurality of radio emitting devices to create a geo-fence within a space and for facilitating determination of a location of a patient device by the radio emitting device and a subset of the plurality of radio emitting devices, the patient device executing a patient application for the space, the facilitating determination of the location occurring when the patient device is moved past the geo-fence and into the space, the determined location relative to the radio emitting device, the radio emitting device transitioning from a sleep state to an active state when the patient device moves within a predetermined distance from the subset of the radio emitting devices.

The invention claimed is:

1. A mobile EMR tracking method comprising:
   creating, by a plurality of devices each comprising a processor and transceiver, a geo-fence within a space, each device capable of communicating with neighboring devices in the plurality and capable of communicating with aggregators in communication with a central server computer over a network;
   determining, by a subset of the plurality of devices, a location of a device executing a patient application for the space when the device is moved past the geo-fence and into the space, the determined location relative to the subset of the devices, each device in the subset transitioning from a sleep state to an active state when the device moves within a predetermined distance from the subset of the devices; and
   executing, by the central server computer upon breaking the geo-fence initiated by a patient using the device, automatic check-in logic, the automatic check-in logic comprising:
   i) relaying the patient's unique ID to a scheduling system at the determined location to perform real time check-in,
   ii) facilitating determination of the patient's identity based on a composite data structure having a data component that is locally encrypted by the patient application and stored on the central server computer,
   iii) sending event based contextual information including the determined patient's identity to an integrated healthcare Administrator system, the healthcare Administrator system informs personnel of the determined location,
   iv) sending EMR information to the device for verification, the EMR information comprises a plurality of RecordSets pertaining to the patient proportionally necessary to support authorized use by the patient application,
   v) applying, by the device, a patient key to the plurality of received RecordSets to determine authorized use, and
   vi) determining authorized use to the received RecordSets via decryption.

2. The method of claim 1, wherein the automatic check-in logic further comprises previewing the patient's identity on the device.

3. The method of claim 2, wherein the automatic check-in logic further comprises making changes to the patient's identity via the patient application on the device.

4. A method for providing granular, context sensitive control over a plurality of RecordSets pertaining to a patient, wherein the plurality of RecordSets are made available via decryption as required and proportionally necessary at any given time to support an authorized use, the method comprising:
   requesting, by a patient application, for a respective portion of a plurality of RecordSets relating to the patient based on a plurality of pseudonymous cipher-based identifiers;
   receiving, from the central server computer, a respective portion of the plurality of RecordSets relating to the patient based on the plurality of pseudonymous cipher-based identifiers; and
   applying, by the patient application, a patient key to the received portion of RecordSets to determine authorized use.

5. The method of claim 4, wherein each one of the plurality of RecordSets comprises an entity name encrypted by a respective RecordSet key in the same RecordSet.

6. The method of claim 1, further comprising providing a meshed network comprising the plurality of devices.

7. The method of claim 1, wherein the event based contextual information is represented as a plurality of JSON structures implemented in a KeyWrap Record.

8. The method of claim 1, wherein the event based contextual information is sent to a distributed queue via a plurality of data channels.

9. A radio emitting device comprising:
   a processor;
   a transceiver for communicating with other radio emitting devices and for communicating with an aggregator in communication with a central server computer over a network; and
   a storage medium for tangibly storing thereon program logic for execution by the processor, the program logic comprising:

radio emitting device communicating logic executed by the processor for communicating with a plurality of radio emitting devices to create a geo-fence within a space and for facilitating determination of a location of a patient device by the radio emitting device and a subset of the plurality of radio emitting devices, the patient device executing a patient application for the facilitating determination of the location occurring when the patient device is moved past the geo-fence and into the space, the determined location relative to the radio emitting device, the radio emitting device transitioning from a sleep state to an active state when the patient device moves within a predetermined distance from the subset of the radio emitting devices, the central server computer, upon breaking the geo-fence initiated by a patient using the patient device, executing automatic check-in logic, the automatic check-in logic comprising:
  i) relaying the patient's unique ID to a scheduling system at the determined location to perform real time check-in,
  ii) facilitating determination of the patient's identity based on a composite data structure having a data component that is locally encrypted by the patient application and stored on the central server computer,
  iii) sending event based contextual information including the determined patient's identity to an integrated healthcare Administrator system, the healthcare Administrator system informs personnel of the determined location,
  iv) sending EMR information to the patient device for verification, the EMR information comprises a plurality of RecordSets pertaining to the patient proportionally necessary to support authorized use by the patient application,
  v) applying, by the patient device, a patient key to the plurality of received RecordSets to determine authorized use, and
  vi) determining authorized use to the received RecordSets via decryption.

10. The radio emitting device of claim 9, wherein the patient application automatically checks a user of the patient device into the space when the patient device moves past the geo-fence.

11. The radio emitting device of claim 9, wherein the automatic check-in logic further comprises previewing the patient's identity on the patient device.

12. The radio emitting device of claim 11, wherein the automatic check-in logic further comprises making changes to the patient's identity via the patient application on the patient device.

13. The radio emitting device of claim 9, wherein the program logic further comprising providing a meshed network comprising the plurality of radio emitting devices.

14. The radio emitting device of claim 9, wherein the event based contextual information is represented as a plurality of JSON structures implemented in a KeyWrap Record.

15. The radio emitting device of claim 9, wherein the event based contextual information is sent to a distributed queue via a plurality of data channels.

16. The method of claim 4, further comprising:
previewing the received portion of RecordSets on the patient application when authorized use is determined via decryption.

17. The method of claim 4, further comprising:
servicing preview when authorized use is determined via decryption by:
  (a) programming the patient application to allow preview, and
  (b) transmitting the received portion of RecordSets to the patient application.

* * * * *